United States Patent [19]

Hara et al.

[11] Patent Number: 5,296,473
[45] Date of Patent: Mar. 22, 1994

[54] PROCESS FOR PREPARING A POWDER HAVING A HIGH CONCENTRATION OF LACTOSUCROSE AND USE OF SAID POWDER

[75] Inventors: Kozo Hara, Kanagawa; Kohki Fujita, Osaka; Masayuki Yamashita; Yasuhiko Tsunetomi, both of Hyogo; Shuzo Sakai, Okayama; Toshio Miyake, Okayama, all of Japan

[73] Assignee: Kabushiki Kaisha Hayashibara Seibutsu Kagaku Kenkyujo, Okayama, Japan

[21] Appl. No.: 850,609

[22] Filed: Mar. 13, 1992

Related U.S. Application Data

[62] Division of Ser. No. 665,828, Mar. 7, 1991, Pat. No. 5,130,239.

[30] Foreign Application Priority Data

Mar. 8, 1990 [JP] Japan ..................... 2-57331

[51] Int. Cl.$^5$ ................. A61K 31/70; A61K 31/715; C12P 19/04
[52] U.S. Cl. ........................ 514/61; 435/72; 435/92; 435/101; 435/244; 435/803; 435/830; 424/464; 514/53; 536/123.1
[58] Field of Search ............... 435/244, 101, 803, 830, 435/72, 97; 424/464; 514/53, 61, 54; 536/123.1

[56] References Cited

U.S. PATENT DOCUMENTS

| | | | |
|---|---|---|---|
| 4,431,737 | 2/1984 | Olivieri et al. | 435/208 |
| 4,617,267 | 12/1986 | Rathbone et al. | 435/97 |
| 4,782,045 | 11/1988 | Machida et al. | 514/61 |
| 4,857,488 | 8/1989 | Kan et al. | 536/123 |
| 5,130,239 | 7/1992 | Hara et al. | 435/97 |
| 5,219,842 | 6/1993 | Okada et al. | 514/53 |

FOREIGN PATENT DOCUMENTS 57-58905 12/1982 Japan.
59-53835 12/1984 Japan.
64-85090 3/1989 Japan.
2-35095 2/1990 Japan.
3-27285 3/1991 Japan.

OTHER PUBLICATIONS

Chem Abs 119(7):71531k (Abs JP05115250 May 14, 1993) Fujimoro.
Derwent Abs 84-092077/15 Biofermin Pharm J59039287 Mar. 3, 1983.
Derwent Abs 88-333867/47 Nisshin Seito KK J63246389 Oct. 13, 1988.
Derwent Abs 89-140776/17 Asahi Chem Ind KK J01085090 Mar. 30, 1987
Derwent Abs 80-68044c/39 Sugimoto et al DE3008668 Sep. 18, 1980.
Gorin, P. A. J. et al. (1965). "Formation of O-$\beta$-D--Glucopyranosyl- and O-$\beta$-D-Galactopyranosyl-Myo-Inositols by Glycosyl Transfer". *Canadian Journal of Chemistry*, vol. 43 (1965), pp. 2259-2264.
"A Color Atlas of Anaerobic Bacteria", pp. 53-65, published by Kabushiki Kaisha Sobunsha, Tokyo, Japan (1964). (Excerpt English translation).
Abstract J59039287 Mar. 1984 Biofermin Phar.

*Primary Examiner*—Herbert J. Lilling
*Attorney, Agent, or Firm*—Browdy and Neimark

[57] ABSTRACT

The lactosucrose high-content powder according to the present invention is prepared by allowing an aqueous solution containing sucrose and lactose to act on a saccharidetransferring enzyme, removing concomitant saccharides in the resultant saccharide solution containing lactosucrose to obtain a solution having a high concentration of lactosucrose, i.e. lactosucrose content of 45 w/w % or more of the sugar composition, and spraydrying the resultant solution to obtain a powder having a high concentration of lactosucrose. The powder is incorporated in an orally- or parenterally-administrable product to obtain an orally- or parenterally-administrable product which exerts a selective growth-promoting-effect on a microorganism of the genus Bifidobacterium in vivo.

7 Claims, 2 Drawing Sheets

PROCESS FOR PREPARING A POWDER HAVING A HIGH CONCENTRATION OF LACTOSUCROSE AND USE OF SAID POWDER

This is a division of application Ser. No. 07/665,828 filed Mar. 7, 1991 now U.S. Pat. No. 5,130,239.

BACKGROUND OF THE INVENTION

1. Field of the invention

The present invention relates to an industrial-scale preparation of a powder having a high concentration of lactosucrose and use of said powder, and, more particularly, to a preparation of a powder having a high concentration of comprising allowing a saccharide-transferring enzyme to act on an aqueous solution containing sucrose and lactose, removing concomitant saccharides from the resultant saccharide solution containing lactosucrose to obtain a solution having a high concentration of a lactosucrose with a lactosucrose content of 45 w/w %, on a dry solid basis (d.s.b.), or higher on sugar composition ("w/w %, d.s.b." will hereinafter be designated as of "w/w %" if not specified otherwise), and spray-drying the solution having a high concentration of lactosucrose into a powder; and to an orally- or parenterallyadministrable product in which the powder is incorporated.

2. Description of the prior art

Lactosucrose is a trisaccharide consisting of galactose, glucose and fructose, and lias the chemical structure shown by O-β-D-Gal-(1→4)-O-α-D-Glc-(1←2)-β-D-Fru (wherein "Gal", "Glc" and "Fru" mean galactose-, glucose- and fructoseresidues). As described in Japanese Patent Publication No.53,835/84, lactosucrose has been known for an extremely useful saccharide as a selective saccharide source for a microorganism of the genus Bifidobacterium.

It has been known that lactosucrose can be prepared by allowing a saccharide-transferring enzyme such as a fructose-transferring enzyme or a galactose-transferring enzyme to act on an aqueous solution containing sucrose and lactose. The fructose-transferring enzymes which have been advantageously used in conventional preparation include, for example, a levansucrase derived from a microorganism such as those of the genera *Bacillus* and *Aerobacter* as described in Japanese Patent Publication Nos.58,905/82 and 53,835/84; and a β-D-fructofuranosidase derived from a microorganism of the genus *Arthrobacter* such as a microorganism of Arthrobacter sp. K-1 (FERM BP-3192 as described in Japanese Patent Application No.160,660/89 which had been applied to Japanese Patent Office on Jun. 26, 1989 by the present inventors. Arthrobacter sp. K-1 was deposited at the Fermentation Research Institute, Agency of Industrial Science and Technology, Ministry of International Trade and Industry, 1-3, Higashi, 1-chome, Tsukuka-shi, Ibaraki-ken 305, Japan, on May 19, 1989. The galactosetransferring enzymes which have been advantageously used in conventional preparation are present, for example, in a micro organism of the genus *Sporoboromyces* as described in *Canadian Journal of Chemistry*, Vol.43, pp.2,259–2,264 (1965), and Japanese Patent Laid-Open No. 85/090-89and in a microorganism of the genus *Rahnella* as described in Japanese Patent Laid-Open No.35,095/90. Intact cells or extracts of such microorganisms can be advantageously used.

It was confirmed that though the content of lactosucrose in a product produced by allowing the enzymes as described above to act on an aqueous solution containing sucrose and lactose was generally in the range of about 5–302, d.s.b., on sugar composition, we could only obtain an unstable powder which readily absorbed moisture and readily solidified to lose its free-flowing ability even when the product was directly dried and pulverized.

SUMMARY OF THE INVENTION

The present inventors studied an industrial-scale preparation of a stable powder containing lactosucrose from a saccharide solution containing lactosucrose formed by using a saccharide-transferring enzyme.

As a result, the present inventors found that an industrial-scale preparation of a stable powder containing lactosucrose was smoothly obtainable by allowing a saccharidetransferring enzyme to act on an aqueous solution containing sucrose and lactose, removing the concomitant saccharides from the resultant lactosucrose solution to obtain a solution having a high concentration lactosucrose with a lactosucrose content of 45 w/w % or higher based on the sugar composition, and spray-drying the solution having a higher concentration of lactosucrose into a powder having a higher concentration of lactosucrose; and that an orally- or parenterally-administrable product containing the powder was easily producible by incorporating the powder in an orally- or parenterally-administrable product.

BRIEF DESCRIPTION OF THE ACCOMPANYING DRAWINGS

Figure 1:
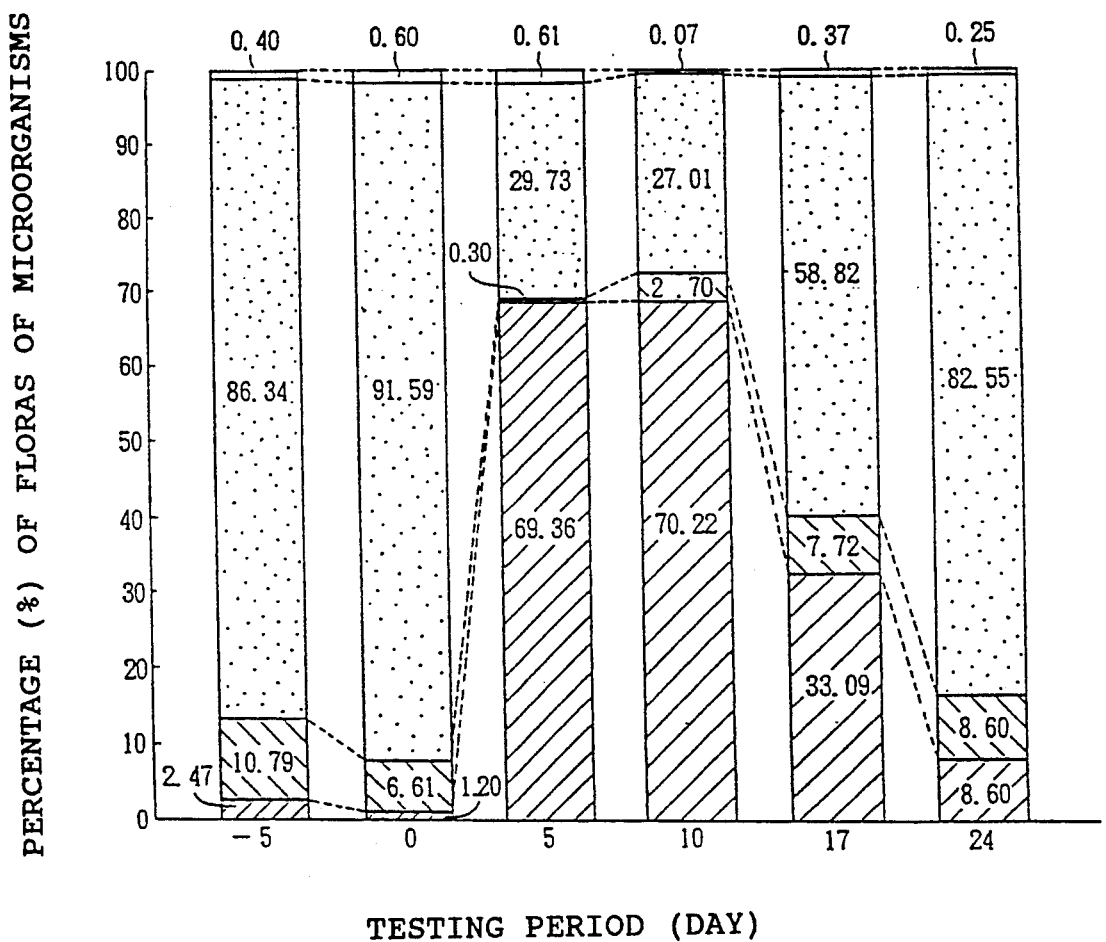
FIG. 1 shows the results of the experiment on intestinal floras.
Figure 2:
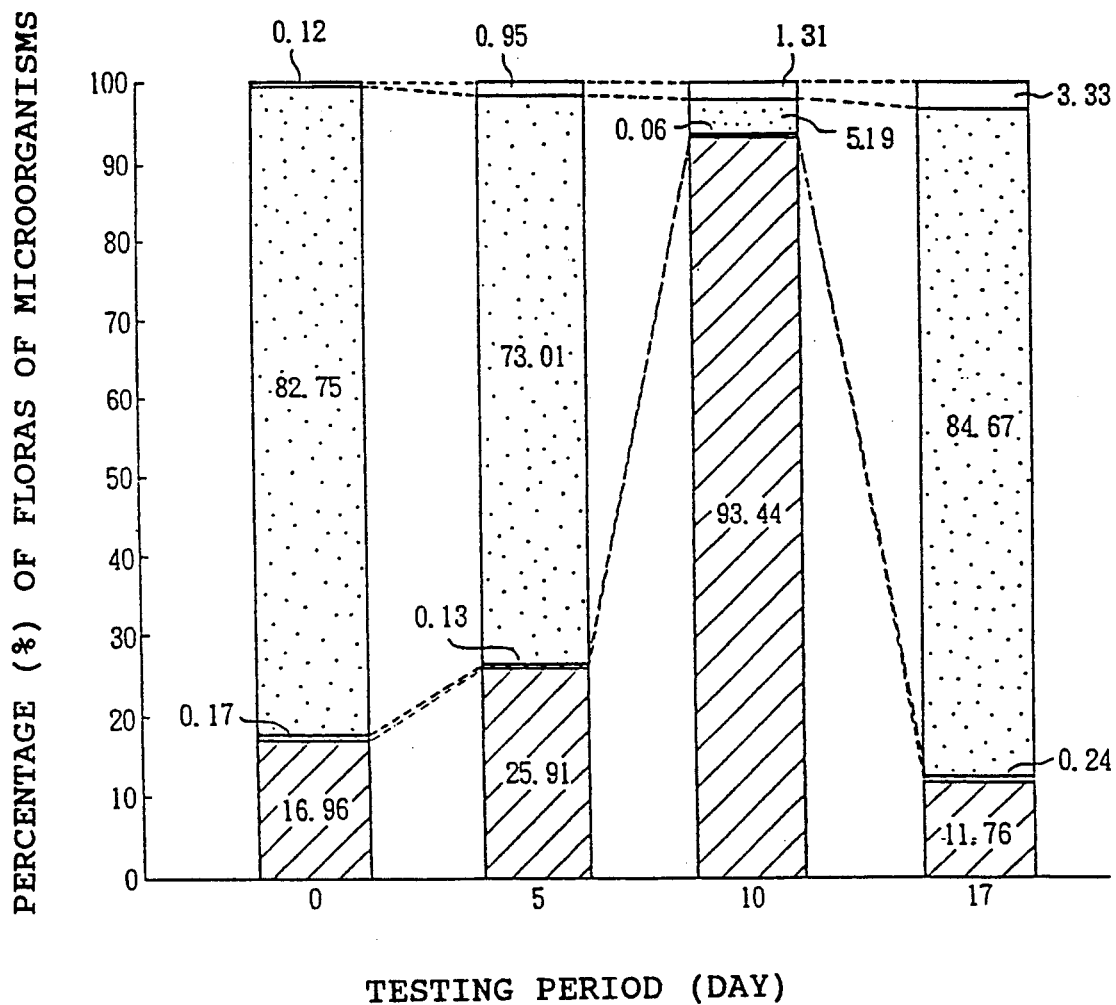
FIG. 2 shows the results of the experiment on intestinal floras.

In FIGS. 1 and 2, ■ shows the floras of the microorganisms of the genera Bifidobacteria, ▪ shows that of the genera Clostridia, ▣ shows that of the genera Bacteroidaceae, and ▫ shows that of the other microorganisms.

DETAILED DESCRIPTION OF THE INVENTION

There has been a great demand for establishing an industrialscale preparation of a stable powder containing lactosucrose for the purpose of extensively using lactosucrose in an orallyor parenterally-administrable product as a saccharide source for a microorganism of the genus Bifidobacterium. Nevertheless, no such preparation has yet been established.

The present inventors studied an industrial-scale preparation of a stable powder containing lactosucrose -from a saccharide solution containing lactosucrose formed by using a saccharide-transferring enzyme, and accomplished the present invention.

The present invention was first effected by allowing a saccharide-transferring enzyme to act on an aqueous solution containing sucrose and lactose to obtain a saccharide solution containing lactosucrose.

The weight ratio and total concentration of sucrose and lactose are generally chosen from a ratio in the range of about 1:10 to 10:1, and a concentration in the range of about 10–60 w/w %. The pH usable in an enzymatic reaction is chosen from a pH of the stable-and optimum-ph of the enzymes used, i.e., a pH in the range of 3–9 in general. The temperature usable in the enzymatic reaction is chosen from a temperature of the stable- and optimum-temperature of the enzymes used, i.e., a temperature in the range of 5°-70° C. in general.

The saccharide-transferring enzymes usable in the invention are, for example, the fructose-transferring enzymes and the galactose-transferring enzymes as described above, and these enzymes can be subjected to an enzymatic reaction in immobilized- or non-immobilized-conditions, followed by the formation of a saccharide solution containing an about 5-30 w/w % lactosucrose on sugar composition.

In order to raise the lactosucrose content in the resultant saccharide solution, either the saccharide solution or a solution which had been prepared in a usual manner by treating the saccharide solution with successive decoloration and salting out, and, if necessary, further concentration, is subjected to one or more purification methods to remove concomitant saccharides, for example, a column chromatography using a strongly-acidic cation exchange resin of alkali-metalor alkaline-earth metal-form, a fermentation method to remove concomitant monosaccharides by using an invertase-defective yeast, and a method to remove concomitant lactose by selectively crystalizing lactose having a relatively low-solubility. Thus, a lactosucrose high-content solution with a lactosucrose content of 45 w/w % or higher based on the sugar composition is obtained.

The strongly-acidic cation exchange resins of alkali-metal- or alkaline-earth metal-form advantageously usable in the invention are one or more styrene-divinylbenzene copolymers bonded with sulfonyl residues in an alkali-metal-form such as $Na^+$- or $K^+$-form, or, in an alkaline-earth metal-form such as $Mg^{++}$- or $Ca^{++}$-form. Examples of commercialized products thereof are "Dowex 50WX1", "Dowex 50WX2" and "Dowex 50WX450", products of Dow Chemical Company, Midland, Michigan, USA; "Amberlite CG-120" and "Amberlite CG-6000", products of Rohm & Haas Company, Phila., Pa., USA; "Amberlite XT-1022E " and "Amberlite XT-1007", products of Tokyo Chemical Industries, Tokyo, Japan; and "Diaion SKLB", "Diaion SK102" and "Diaion SK104", products of Mitsubishi Chemical Industries Ltd., Tokyo, Japan.

The column chromatography usable in the invention will hereinafter be described more concretely: A strongly-acidic cation exchange resin of alkali-metal- or alkaline-earth metal-form is suspended in water, and the resultant is packed in a column to give a total gel-bed depth of 3 m or longer, or preferably, 5 m or longer. A saccharide solution containing lactosucrose as the material, which has been adjusted to a concentration of 40-70 w/w is added to the column in a volume of about 1-50 v/v % against the resin while keeping the inner temperature of the column at a temperature in the range of about 30°-70° C., and the column was fed with water at a flow-rate of in about SV 0.1-2.0 by the upstream or the downstream method to effect elution and fractionation. Thus, an objective lactosucrose high-content fraction with a lactosucrose content of 45 w/w % or higher based on sugar composition was obtained.

In the column chromatography as described above, a fraction having a low concentration of lactosucrose can be advantageously recovered besides the lactosucrose high-content fraction, and a portion of the elution water can be replaced with the fraction having a low concentration of lactosucrose in the next chromatography procedure. For example, a high yield of a preparation of a solution havng a high concentration of lactosucrose can be advantageously obtained by successively feeding to a column as the starting material a saccharide solution having a low concentration of lactosucrose low-content fraction, and elution water to effect fractionation.

Intact saccharide solutionhaving a high concentration of lactosucrose thus obtained, or, if necessary, a solution which had been prepared by treating the saccharide solution in a usual manner with successive decoloration, salting out and concentration, is spray-dried to form a powder having a high concentration of lactosucrose. The spray-drying methods favorably usable in the invention are, for example, conventional methods using a rotating-disc, pressure nozzle or twin-fluid nozzle.

It was confirmed that the powder having a high concentration of lactosucrose so obtained, with a lactosucrose content of 45 w/w % or more based upon on sugar composition, was a relatively low-hygroscopicand stable-powder having a satisfactory free-flowing ability in its poured angle of repose, drained angle of repose, and angle of slide. It was also confirmed that the powder alone or in combination with other appropriate substances can be formed into a powder, or, if necessary, into a granule, sphere, short-length of rod, cube or tablet. The products thus obtained can be extensively used in an orally- or parenterallyadministrable product as a selective saccharide source for a microorganism of the genus Bifidobacterium, as well as a sweetener, filler, stabilizer, viscosity-imparting agent, crystalization-preventive agent for saccharide, humectant and bulking agent.

More particularly, since the powder of the present invention has a delicate sweetness and about half the sweetening power of sucrose, and satisfiably harmonizes with substances having other tastes of, for example, sour, saltiness, astringency, deliciousness and bitterness, the powder can be advantageously used as a sweetener and taste-improving agent, as well as a selective saccharide source for a microorganism of the genus Bifidobacterium in seasonings, foods, beverages, cigarettes and tobaccos. Furthermore, the powder can be used in feeds and pet foods for animals such as domestic animals, fowls, honey bees, silk worms and fishes as a selective saccharide source for a microorganism of the genus Bifidobacterium, as well as an agent for improving taste quality of the feeds and pet foods.

In addition,.the powder can be advantageously used as a selective saccharide source for a microorganism of the genus Bifidobacterium, as well as a sweetener, flavor-imparting agent, filler, stabilizer and viscosity-imparting agent in cosmetics and pharmaceuticals, for example, medicine for internal administration, intubation nutrition, troche, liver oil drop, agent containing a living microorganism, medicine for intestinal disorders, oral refrigerant and cachou.

As described, above, the wording "an orally- or parenterally-administrable product" as referred to in the invention includes those which can be orally- or parenterallyused, for example, sweeteners, foods, beverages, feeds, pet foods, pharmaceuticals and cosmetics in which the powder having a high concentration of lactosucrose of the invention is incorporated.

Furthermore, the wording "incorporating powder having a high concentration of lactosucrose as referred to in the invention means that the powder having a high concentration of lactosucrose can be incorporated in an orally- or parenterally-administrable product before the completion of its processing. Examples of such processes favorably usable in the invention are conventional methods, for example, mixing, kneading, dissolving, soaking, permeating, spreading, applying, spraying and injecting.

When an orally- or parenterally-administrable product, in which the lactosucrose high-content powder is incorporated, is used as a selective saccharide source for a microorganism of the genus Bifidobacterium, the product is favorably administered at a dose in the range of 0.01–5.0 g/day, based on the weight of lactosucrose, per kg of the weight of a recipient, i.e., human or animal. It is favorable for the recipient to take the product at the dose specified above every day or every other day. In this case, lactosucrose is not substantially digested and assimilated until it reaches the intestine, but is selectively utilized mainly in the large intestine by a microorganism of the genus Bifidobacterium, followed by the growth of the microorganism.

Thus, since lactosucrose, when it is taken, scarcely causes an increase of the blood sugar content and stimulates the secretion of insulin, lactosucrose is substantially a low-caloric sweetener or a dietary sweetener. In general, when we expect a high selective growth-promoting-effect on a microorganism of the genus Bifidobacterium in the orally- or parenterally-administrable product according to the present invention, it is favorably carried out to incorporate the lactosucrose powder of the present invention in an orally- or parenterally-administrable product in an amount of about 0.1 w/w % or more, preferably in an amount of 0.5 w/w % or higher based on the weight of lactosucrose.

The selective growth of a microorganism of the genus Bifidobacterium causes the formation of organic acids such as acetic acid and tactic acid to lower the pH in a large intestine, and inhibits the growth of harmful bacteria such as putrefactive bacteria and those which cause spontaneous infection. Furthermore, the selective growth inhibits the formation of harmful substances such as ammonia, indole and cresol, and exerts an efficacy or intestinal disorders by adequately stimulating the intestines and promoting peristalsis. Based on these functions of lactosucrose, a powder having a high concentratoin of lactosucrose or an orally- or parenterallyadministrable product in which the powder is incorporated can play a role in the control and promotion of health and beauty, and can be advantageously used in the prevention of geriatric diseases such as diabetes, hypertension and large bowel cancer, the promotion of recovery of health during or after diseases, and the prevention and treatment of hyperammonemia and hepatic encephalopathy. Furthermore, the powder and product can be advantageously used for animals such as domestic animals and fowls in the prevention of infection and diarrhea, the inhibition of unpleasant smell caused by feces, and the promotion of appetite, weight gain and egg-laying.

The present invention will hereinafter be explained by the following Experiments.

EXPERIMENT 1

Preparation of saccharide solution having a high concentration of lactosucrose by using saccharide-transferring enzyme

EXPERIMENT 1

Preparation of levansucrase

Sixty liters of a liquid medium containing 3 w/v % defatted soybean, 2 w/v % glucose, 4 w/v % sucrose, 0.6 w/v % $(NH_4)_2HPO_4$ 0.03 w/v % $MGSO_4.4H_2O$, 0.02 w/v% KCl, 0.02 w/v % $CA(CH_3COO)_2$ 0.001 w/v % $MnSO_4 4H_2O$ and water was adjusted to pH 7.0, sterilized at 120° C. for 20 minutes, and cooled. To the resultant liquid medium a seed culture of *Bacillus subtiles* (ATCC 6051) was inoculated, and cultured at 37° C. for 3 days under aeration-agitation conditions. After completion of the culture, the resultant culture medium was centrifuged to obtain a supernatant, which was then added with an equimolar precooled ethanol. The resultant precipitate was centrifugally collected and dissolved in 20mM acetic acid buffer (pH 5.0) containing 1 mM $CaCl_2$. The mixture solution was dialyzed overnight against fresh acetic acid buffer, and the resultant solution was centrifuged to obtain a supernatant, which was then applied to a column packed with DEAE-cellulose to adsorb levansucrase. The column was washed with fresh acetic acid buffer, and eluted with fresh acetic acid buffer containing 1M NaCl to obtain an eluate, which was then added with $(NH_4)_2SO_4$ so to give a 90% saturation. The resultant precipitate was centrifugally collected, and dissolved in 500 ml of fresh acetic acid buffer to obtain a levansucrase solution having a levansucrase activity of about 120 units/ml.

The assay of levansucrase activity is as follows: Two ml of a reaction mixture (pH 7.0) containing 10 w/v % sucrose, 50 mM phosphate buffer and a levansucrase specimen, is incubated at 30° C. After 30 minutes of incubation, the resultant mixture was heated to inactivate the enzyme, and the amount of glucose formed was determined by the glucose oxidaseperoxidase coupled system. One unit of levansucrase activity is defined as the amount of enzyme that forms one limol of glucose per minute under the above conditions.

EXPERIMENT 1-2

Preparation of saccharide solution containing lactosucrose

Five parts by weight of sucrose and 3 parts by weight of lactose were dissolved by heating in 9 parts by weight of water. The resultant solution was cooled to 40° C. and added with a levansucrase specimen prepared by the method in Experiment 1-1 in an amount of one unit per g of sucrose. The mixture was enzymatically reacted at 40° C. and pH 7.0 for 24 hours. After completion of the reaction, the resultant mixture was heated to inactivate the enzyme and filtered. The filtrate was decolored in a conventional manner with activated charcoal and salted out with an ion-exchange resin of H- or OH-form. The resultant solution was concentrated to obtain a saccharide solution with a concentration of about 60 w/w %. The saccharide solution was a mixed solution of saccharides comprising glucose, fructose, sucrose, lactose and lactosucrose, wherein the content of lactosucrose in the saccharide solution was about 25 w/w % on sugar composition, and we could only obtain an unstable powder with a strong hygroscopicity even when the saccharide solution was directly spray-dried.

EXPERIMENT 2

Lactosucrose content in powder containing thereof and its influence on stability of said powder In this experiment, the saccharide solution containing lactosucrose in Experiment 1-2 was used as the starting material.

"Amberlite XT-1007 (Na+form, polymerization degree of 6%)", an alkali-metal strongly-acidic action exchange resin, commercialized by Tokyo Chemical Company, Tokyo, Japan, was used as the resin for fractionation. The resin was first suspended in water and then packed in jacketted stainlesscolumns having an inner diameter of 5.4 cm. Two columns were cascaded to give a total gel-bed depth of 10 m in order to flow a feed solution in series. The columns were added with the saccharide solution in an amount of 5 v/v % against the resin while keeping the inner temperature of the columns at 55° C., and fed with a 55° C. hot water at a flow rate of SV 0.5 to effect fractionation. Thus, varieties of lactosucrose high-content solutions were obtained, and subjected in a usual manner to decoloration, salting out, concentration and spray-drying to obtain powders with a moisture content of lower than 2 w/w In order to evaluate or determine the level of moisture absorbency (increase of weight), the free-flowing ability, and the presence of solidification, a variety of lactosucrose powder was placed in an aluminum vessel, and allowed to stand for 2 days under a condition of a relative humidity of 50% and a temperature of 25° C. The angles of repose, i.e., poured angle of repose, drained angle of repose, and angle of slide, were measured to quantitatively evaluate the level of freeflowing ability of each lactosucrose powder. The poured angle of repose was measured by keeping a funnel made of polystyrene 110 mm in diameter of its cylindrical part, 20 mm in length of its cylindrical part, 100 mm in height of its conic part, and 10 mm in diameter of its discharge pipe, at a position of 80 mm from a floor to the lower end of the discharge pipe; naturally falling down from the funnel a variety of lactosucrose powder filled in the funnel; and measuring the angle of the falling substance. The drained angle of repose was determined by measuring the angle of a variety of lactosucrose powder which remained in a cylindrical vessel made of polystyrene 80 mm in diameter, 40 mm in height, and an opening of 25 mm in diameter at the bottom, after the exhaustion of the powder from the opening. The angle of slide was measured by placing 10 g of a variety of lactosucrose powder on the surface of a glass plate having 95 mm in length, 40 mm in wide, and 5 mm in thickness; gradually slanting the plate; and measuring the angle of the plate when the powder began to slide. The results were as shown in Table.

EXPERIMENT 3

Influence of lactosucrose high-content powder on human intestinal floras

In order to confirm whether a lactosucrose highcontent powder was useful as a selective saccharide source for a microorganism of the genus Bifidobacterium in vivo, a powder with a lactosucrose content of about 55% on sugar composition, obtained by the method in Experiment 2, was orally administered to 2 healthy volunteers (47-years-old men) at 3-4 times a day in an amount 20 g/adult/day for successive 10 days. Intestinal floras were detected by first recovery feces, then immediately weighing one g of the feces, followed by suspending the resultant in 9 ml of a diluent, and checking intestinal floras in terms of the genera according to the method described in Tomotari Mitsuoka, *A Color Atlas of Anaerobic Bacteria*, pp.53–65 (1984), published by Kabushiki Kaisha Sobunsha, Tokyo, Japan. The detection of intestinal floras was carried out once or twice before the administrations, twice at fifth- and tenth-day during the administrations, and once or twice after completion of the administrations.

The results obtained from the two volunteers were respectively shown in FIGS. 1 and 2.

As evident from these FIGS., the administrations of the lactosucrose high-content powder significantly influenced the intestinal floras of the volunteers. Especially, such administrations increased the number of the microorganisms of the genera Bifidobacteria, but decreased the number of the microorganisms of the genera Bacteroidaceae.

As a result, after the successive 10 days administrations, the percentage of the floras of the microorganisms of the genera Bifidobacteria against the total floras of microorganisms increased to 70.22% from 1.20% in the volunteer shown in FIG. 1, and to 93.44% from 16.96% in the volunteer shown in FIG. 2. No symptom such as abdominal pain, diarrhea, meteorism, constipation or dysphoria was observed over the period of the administrations.

Thus, the lactosucrose high-content powder according to the present invention can be advantageously used as a selective saccharide source for a microorganism of the genus Bifidobacterium.

Examples A and B will respectively explain a lactosucrose high-content powder and an orally- or parenteral-

TABLE

| Lactosucrose (w/w %) | Increase of weight (w/w %) | Free-flowing ability | Solidification | Poured angle of repose (°) | Drained angle of repose (°) | Angle of slide (°) | Judgement |
| --- | --- | --- | --- | --- | --- | --- | --- |
| 25 | 15.8 | Unfavorable | Present | Impossible | Impossible | Impossible | Control |
| 35 | 11.3 | Unfavorable | Present | Difficult | Difficult | Difficult | Control |
| 45 | 4.0 | Satisfactory | not present | 45 | 48 | 56 | Present invention |
| 55 | 2.9 | Satisfactory | not present | 42 | 41 | 51 | Present invention |
| 75 | 2.5 | Satisfactory | not present | 40 | 40 | 49 | Present invention |
| 85 | 2.4 | Satisfactory | not present | 40 | 39 | 49 | Present invention |

Note: In Table, the wordings "Impossible" and "Difficult" respectively mean that the measurements are impossible and difficult.

As evident from the results in Table, it was confirmed that a powder having a high concentration lactosucrose with a lactosucrose content of 45 w/w % or higher based on sugar composition was easily handleable because it had a relatively low-hygroscopicity and a satisfiable stability.

ly-administrable product in which the powder is incorporated.

EXAMPLE A-1

Lactosucrose Powder having a high concentration of

Three parts by weight of sucrose and 3 parts by weight of lactose were dissolved by heating in 10 parts by weight of water, and the mixture was cooled to 40°

C., added with a levansucrase specimen prepared by the method in Experiment 1-1 in an amount of 1.5 units per g of sucrose, and subjected to an enzymatic reaction at 40° C. and pH 6.0 for 16 hours. After completion of the enzymatic reaction, the resultant mixture was heated to inactivate the enzyme and filtered. The filtrate was in decolored in a conventional manner with activated charcoal, and salted out with an ion-exchange resin of H- or OH-form. The resultant solution was concentrated into a saccharide solution with a concentration of about 50 w/w %. The saccharide solution contained about 30 w/w % lactosucrose based on sugar composition.

"Dowex 50WX4 (K+- form, polymerization degree of 4%)", an alkali-metal strongly-acidic cation exchange resin, commercialized by Dow Chemical Company, Midland, Michigan, USA, which was used as the resin for fractionation, was first suspended in water, then packed in jacketted stainless-columns having an inner diameter of 5.4 cm. Four columns were cascaded to give a total gel-bed depth of 8 m in order to flow a feed solution in series. About 10 v/v % of the saccharide solution against the resin was added while keeping the inner temperature of the columns at 60° C., and fractionated by feeding 60° C. water to the columns at a flow-rate of an about SV 0.3 to obtain a solution containing about 50 w/w % lactosucrose based on sugar composition. The solution thus obtained was decolored, salted out, concentrated and spray dried in a conventional manner into a powder with a moisture content of lower than 2 w/w % in the yield of about 50%.

Since the powder has a relatively low-hygroscopicity, excellent free-flowing ability and stability, the powder is easily handleable.

The powder can be advantageously used alone or in combination with other appropriate substances in orally- or parenterally-administrable products as a selective saccharide source for a microorganism of the genus Bifidobacterium, as well as a sweetener,, filler, and viscosity-imparting agent.

EXAMPLE A-2

Lactosucrose Powder having a high concentration of

Similarly as in Example A-1 except for using as the resin for fractionation "Diaion SK104 (Ca++- form, polymerization degree of 4%)", an alkaline-earth metal strongly-acidic cation exchange resin, commercialized by Mitsubishi Chemical Industries, Ltd., Tokyo, Japan, a saccharide solution containing an about 30 w/w % lactosucrose obtained by the method in Example A-1 was fractionated to obtain a solution containing an about 75 w/w % lactosucrose on sugar composition, which was further decolored, salted out, concentrated and spray-dried into a powder with a moisture content of lower than 2 w/w % in the yield of about 30%.

Since the powder has a relatively low-hygroscopicity, excellent free-flowing ability and stability, the powder is easily handleable.

Similarly as the powder in Example A-1, the powder can be advantageously used alone or in combination with other appropriate substances in orally- or parenterally-administrable products as a selective saccharide source for a microorganism of the genus Bifidobacterium, as well as a sweetener, filler, and viscosity-imparting agent.

EXAMPLE A-3

Lactosucrose Powder having a high concentration of

Example A-3(1)

A seed culture of a microorganism of Arthrobacter sp. K-1 (FERM BP 3192 was inoculated to a slant nutrient agar medium, and cultured at 37° C. for 2 days. Thereafter, a small amount of the microorganisms grown on the medium was collected with a platinum loop, inoculated to 500-ml-volume of shaking flasks, which had been first distributed with 60 ml aliquots of a liquid medium (pH 7.0) containing 1.2 w/v I yeast extract, 0.8 w/v % polypeptone, 4 w/v % soluble starch, 0.4 w/v % (NH$_4$)$_2$ HPO$_4$, 0.1 W/V % MgSO$_4$7H$_2$O and water, then sterilized, and cultured at 37° C. for 5 days under shaking conditions. After completion of the culture, the resultant liquid medium was centrifuged to obtain about 1.1 L of a supernatant containing β-D-fructofuranosidase. The supernatant as an enzyme solution showed a β-D-fructofuranosidase activity of about 30 units/ml.

The assay of β-D-fructofuranosidase activity is as follows: Two hundred μL of 20% sucrose solution containing 40% xylose in 500 mM phosphate buffer (pH 6.5) is added with 200 μL of an appropriately prediluted enzyme solution, and the mixture is incubated at 40° C. for 10 minutes. A portion of the resultant mixture sampled in a vessel is placed in boiling water to activate the enzyme, and the amounts of the liberated glucose and fructose are determined with "F-Kit", a reagent for enzymatic food analysis, commercialized by Boehringer Mannheim Yamanouchi KK, Tokyo, Japan. The amount of the transferred fructose is determined by the amount of the liberated glucose minus that of fructose. One unit of β-Dfructofuranosidase activity is defined as the amount of enzyme that transfers one μmol of fructose per minute.

EXAMPLE A-3(2)

One part by weight of sucrose and one part by weight of lactose were dissolved by heating in 3 parts by weight of water, and the mixture was cooled to 50° C., added with a β-Dfructofuranosidase specimen prepared by the method in Example A-3(1) in an amount of 5 units per g of sucrose, and subjected to an enzymatic reaction at 50° C. and pH 6.5 for 5 hours. Thereafter, the resultant mixture was heated to inactivate the enzyme and filtered. The filtrate was decolored in a conventional manner, salted out and concentrated into an about 60 w/w % saccharide solution containing an about 30 w/w % lactosucrose on sugar composition.

Similarly as in Example A-1 except for replacing the resin used in Example A-2 with an alkaline-earth metal strongly-acidic cation exchange resin of Mg++-form as the resin for fractionation, the saccharide solution was fractionated to obtain a solution containing about 55 w/w % lactosucrose based on sugar composition, which was further purified, concentrated and spray-dried into a powder with a moisture content of lower than 2 w/w % in a yield of about 45%.

Since the powder has a relatively low-hygroscopicity, excellent free-flowing ability and stability, the powder is easily handleable.

Similarly as the powder in Example A-1, the powder can be advantageously used alone or in combination with other appropriate substances in orally- or parenterally-administrable products as a selective saccharide source for a microorganism of the genus Bifidobacterium, as well as a sweetener, filler, and viscosity-imparting agent.

EXAMPLE A-4

Lactosucrose powder having a high concentration of

Similarly as in Example A-1 except for using as the resin for fractionation "Amberlite CG-6000 (Na+-form, polymerization degree of 6%)", an alkali-metal strongly-acidic cation exchange resin, commercialized by Rohm & Haas Company, Phila., Pa., USA, a saccharide solution containing about 30 w/w % lactosucrose obtained by the method in Example A-3 was fractionated to obtain a solution containing about 70 w/w lactosucrose based on sugar composition, which was further purified, concentrated and spray-dried into a powder with a moisture content of less than 2 w/w % in a yield of about 35%.

Since the powder has a relatively low-hygroscopicity, excellent free-flowing ability and stability, the powder is easily handleable.

Similarly as the powder in Example A-1, the powder can be advantageously used alone or in combination with other appropriate substances in orally- or parenterally-administrable products as a selective saccharide source for a microorganism of the genus Bifidobacterium, as well as a sweetener, filler, and viscosity-imparting agent.

EXAMPLE A-5

Lactosucrose powder having a high concentration of

One part by weight of sucrose and one part by weight lactose were dissolved by heating in 2 parts by weight of water, and the mixture was cooled to 50° C., added with a β-Dfructofuranosidase specimen prepared by the method in Example A-3(1) in an amount of 8 units per g of sucrose, and subjected to an enzymatic reaction at 50° C. and pH 6.0 for 20 hours. The resultant mixture was further heated to inactivate the enzyme and filtered to obtain a filtrate.

The filtrate contained an about 35 w/w % lactosucrose based on sugar composition together with concomitant saccharides, for example, monosaccharides such as glucose and fructose, and oligosaccharides such as lactose and sucrose.

The filtrate was adjusted to give a saccharide concentration of about 30 w/w %, and the resultant solution was added with an invertase-defective yeast with a moisture content of about 65%, commercialized by Oriental Yeast Co. Ltd., Tokyo, Japan, in an amount of 5 w/w % against saccharide, d.s.b. The mixture was adjusted to a pH in the range of 6.5–7.0, and fermented at 30° C. for 24 hours in order to assimilate the monosaccharides in the mixture to obtain a solution containing about 46 w/w % lactosucrose on sugar composition. The solution thus obtained was in an usual manner decolored, salted out, concentrated and spray-dried into a powder with a moisture content of lower 3% in the yield of about 64%.

Since the powder has a relatively low-hygroscopicity, excellent free-flowing ability and stability, the powder is easily handleable.

Similarly as the powder in Example A-1, the powder can be advantageously used alone or in combination with other appropriate substances in orally- or parenterally-administrable products as a selective saccharide source for a microorganism of the genus Bifidobacterium, as well as a sweetener, filler, and viscosity-imparting agent.

EXAMPLE A-6

Lactosucrose high-content powder

A saccharide solution containing an about 35 w/w % lactosucrose, obtained by the method in Example A-5, was concentrated into an about 78 w/w % solution, which was further added at 50° C. with a small amount of a crystalline lactose as the seed crystal, and gradually cooled to 30° C. under stirring conditions in order to crystalize lactose. The resultant mixture was centrifuged and filtered in order to remove the crystallized lactose to obtain a filtrate containing about 46 w/w % lactosucrose based on sugar composition, which was further decolored, salted out, concentrated and spray-dried in a conventional manner into a powder with a moisture content of less than 3% in a yield of about 66%.

Since the powder has a relatively low-hygroscopicity, excellent free-flowing ability and stability, the powder is easily handleable.

Similarly as the powder in Example A-1, the powder can be advantageously used alone or in combination with other appropriate substances in orally- or parenterally-administrable products as a selective saccharide source for a microorganism of the genus Bifidobacterium, as well as a sweetener, filler, and viscosity-imparting agent.

EXAMPLE A-7

Lactosucrose powder having a high concentration of

Four parts bu weight of sucrose and 5 parts by weight of lactose were dissolved by heating in 13.5 parts by weight of water, and the solution cooled to 55° C. and added with a β-D-fructofuranosidase specimen prepared by the method in Example A-3(1) in an amount of 10 units per g of sucrose. The mixture was subjected to an enzymatic reaction at 55° C. and pH 6.5 for 15 hours. The resultant mixture was heated to inactivate the enzyme and filtered to obtain a filtrate.

The filtrate contained about 33 w/w % lactosucrose based on sugar composition together with concomitant saccharides, for example, monosaccharides such as glucose and fructose, and oligosaccharides such as lactose and sucrose.

The filtrate was concentrated into an about 78 w/w % solution, which was then added at 50° C. under stirring conditions with a small amount of a crystalline lactose as the seed crystal to crystalize lactose. The resultant mixture was filtered to remove the crystallized lactose. The filtrate thus obtained was adjusted to give an about 30 w/w % solution, and, similarly as in Example A-5, concomitant monosaccharides in the resultant solution were assimilated by the fermentation using an invertase-defective yeast to obtain a solution containing an about 50 w/w % lactosucrose on sugar composition. The solution thus obtained was decolored, salted out, concentrated and spray-dried in a conventional manner into a powder with a moisture content of less than 2% in a yield of about 52%.

Since tile powder has a relatively low-hygroscopicity, excellent free-flowing ability and stability, the powder is easily handleable.

Similarly as the powder in Example A-1, the powder can be advantageously used alone or in combination with other appropriate substances in orally- or parenterally-administrable products as a selective saccharide source for a microorganism of the genus Bifidobacterium, as well as a sweetener, filler, and viscosity-imparting agent.

EXAMPLE B-1

Mixed sweetener

One part by weight of a powder having a high concentration of a lactosucrose obtained by the method in Example A-2, was mixed to homogeneity with 0.05 parts by weight of "α-G sweet", a sweetener commercialized by Toyo Sugar Refining Co., Ltd., Tokyo, Japan, to obtain a pulverized sweetener. The product has a delicate sweetness and about twice the sweetening power of sucrose. Furthermore, the product exerts a growthpromoting-effect on a microorganism of the genus Bifidobacterium, and can be advantageously used in the control and promotion of health and beauty, the prevention of geriatric diseases, the promotion of recovery of health during and after diseases, and the prevention and treatment for hyperammonemia and hepatic encephalopathy. In addition, the product can be advantageously used for animals such as domestic animals and fowls in the prevention of infection and diarrhea, the promotion of appetite and fatting, and inhibition of unpleasant smell caused by feces.

EXAMPLE B-2

Hard candy

Fifteen parts by weight of a powder having a high concentration of lactosucrose obtained by the method in Example A-1 was dissolved by heating in 95 parts by weight of a hydrogenated maltose syrup with a moisture content of 25%, and the mixture was concentrated under a reduced pressure until it gave a moisture content of less than 2 w/w %. The resultant was mixed with one part by weight of citric acid and an adequate amount of lemon flavor and coloring a nt, and the mixture was formed into a hard candy in a conventional manner.

The product is a low-cariogenic hard candy having a delicate sweetness. Furthermore, the product exerts a growthpromoting-effect on a microorganism of the genus Bifidobacterium, and, similarly as the product in Example B-1, the product can be advantageously used in the control and promotion of health and beauty, the prevention of geriatric disease, the promotion of recovery of health during and after diseases, and the prevention and treatment of diseases.

EXAMPLE B-3

Chewing gum

Two parts by weight of a gum base was heated to a level that it softened, which was further admixed with 4 parts by weight of a powder having a high concentration of a lactosucrose obtained by the method in Example A-3, 3 parts by weight of glucose, and an adequate amount of mint flavor and coloring agent. The resultant mixture was in an usual manner kneaded with a roll and formed into a chewing gum.

The product is satisfactory in its texture and sweetness. Furthermore, the product exerts a growth-promotingeffect on a microorganism of the genus Bifidobacterium, and, similarly as the product in Example B-1, the product can be advantageously used in the control and promotion of health and beauty, the prevention of geriatric disease, the promotion of recovery of health during and after diseases, and the prevention and treatment of diseases.

EXAMPLE B-4

Chocolate

Forty parts by weight of cacao paste, 10 parts by weight of cacao butter, 15 parts by weight of a having a high concentration of lactosucrose obtained by the method in Example A-4, 10 parts by weight of sucrose, and 15 parts by weight of whole milk powder were mixed and passed through a refiner. After the degree of fineness of the mixture, the resultant was subjected to a conche and added with 0.5 parts by weight of lecithin. The resultant mixture was kneaded up at 50° C. for 2 days, fed into a molder, and solidified to obtain a chocolate.

The product has a satisfactory taste, flavor and meltability when it is placed on the tongue, as well as having no fear of causing fat- and sugar-blooms. Furthermore, the product exerts a growth-promoting-effect on a microorganism of the genus Bifidobacterium, and, similarly as the product in Example B-1, the product can be used in the control and promotion of health and beauty, and the promotion of recovery of health during and after diseases.

EXAMPLE B-5

Lactic acid beverage

Seventy parts by weight of a coffee extract, 110 parts by weight of milk, 14 parts by weight of a having a high concentration of lactosucrose obtained by the method in Example A-5, and an adequate amount of coffee flavor and coloring agent were mixed to homogeneity, and the mixture was sterilized, cooled, injected, and packed in a conventional manner to obtain a lactic acid beverage.

The product is a milk of coffee having a satisfactory flavor and taste. Furthermore, the product exerts a growthpromoting-effect on a microorganism of the genus Bifidobacterium, and, similarly as the product in Example B-1, the product can be advantageously used in the control and promotion of health beauty, the prevention of geriatric diseases, and the promotion of recovery of health during and after diseases.

EXAMPLE B-6

Custard cream

Five hundred parts by weight of corn starch, 500 parts by weight of a powder having a high concentration of lactosucrose obtained by the method in Example A-6, 5 parts by weight of salt, and 400 parts by weight of "SUNMALT®", a maltose powder, commercialized by Hayashibara Co., Ltd., Okayama, Japan, were passed through a sieve and mixed to homogeneity. The resultant was admixed with 1,400 parts by weight of egg, and the mixture was gradually poured with 5,000 parts by weight of a boiling milk. The resultant mixture was further subjected to a gentle heating under stirring conditions, and the heating was stopped when the corn starch was completely gelatinized to show a homogeneous semi-transparency. Thereafter, the resultant mixture was cooled and added with an adequate amount of vanilla essence to obtain a custard cream.

The product has a smooth surface and gloss, moderate sweetness and satisfactory taste. Furthermore, the product exerts a growth-promoting-effect on a microorganism of the genus Bifidobacterium, and, similarly as the product in Example B-1, the product can be advantageously used in the control and promotion of health and beauty, the prevention of geriatric diseases, and the promotion of recovery of health during and after diseases.

EXAMPLE B-7

Ready-mix corn potage

Thirty parts by weight of a pregelatinized corn powder, 5 parts by weight of a pregelatinized starch, 4 parts by weight of a pregelatinized potato starch, 12 part s by weight of a pregelatinized waxy corn starch, 8 parts by weight of a powder having a high concentration of lactosucrose obtained by the method in Example A-7, 5 parts by weight of sodium glutamate, 8.5 parts by weight of salt, 7 parts by weight of defatted milk, and 0.5 parts by weight of onion powder were grinded to homogeneity. The resultant was admixed with 0.5 parts by weight of sorbitan fatty acid ester and 9 parts by weight of plant hardened oil which had been melted by heating. The mixture was admixed with 10 parts by weight of lactose. The resultant mixture was granulated by subjecting it to a fluidized-bed granulator while spraying it a small amount of water. The resultant granules were dried with a 70° C. hot-air and separated with a sieve to obtain a ready-mix corn potage.

When the product is poured with a boiling water, the product is readily dissolved and dispersed to obtain a soup having an excellent taste and flavor. Furthermore, the product exerts a growth-promoting-effect on a microorganism of the genus Bifidobacterium, and, similarly as the product in Example B-1, the product can be advantageously used in the control and promotion of health and beauty, the prevention of geriatric diseases, and the promotion of recovery of health during and after diseases.

EXAMPLE B-8

Intubation nutrient

A composition containing 580 parts by weight of a powder having a high concentration of lactosucrose obtained by the method in Example A-1, 190 parts by weight of dried yolk, 209 parts by weight of defatted milk, 4.4 parts by weight of sodium chloride, 1.85 parts by weight of potassium chloride, 4 parts by weight of magnesium sulfate, 0.01 part by weight of thiamine, 0.1 part by weight of sodium ascorbate, 0.6 parts by weight of vitamin E acetate, and 0.04 part by weight of nicotinamide, was prepared. Twenty-five g aliquots of the composition were distributed into laminated-aluminum small bags, and heat sealed to obtain an intubation nutrient in solid.

The quality of the product is stably retained for a relatively long period, and its solubility and dispersibility in a solvent are excellent.

In use, one bag of the product is first dissolved in an about 150–300 ml water to prepare an intubation nutrient solution, which is then administered by intubation feeding, for example, into the nasal cavity, gullet and stomach. Furthermore, the product exerts a growth-promoting-effect on a microorganism of the genus Bifidobacterium. Similarly as the product in Example B-1, the product can be advantageously used in tile control and promotion of health and beauty, the prevention of geriatric diseases, and the promotion of recovery of health during and after diseases.

EXAMPLE B-9

Tablet

Forty parts by weight of a powder having a high concentration of lactosucrose obtained by the method in Example A-2, 10 parts by weight of maltose, one part by weight of calcium phosphate tribasic, one part by weight of sugar ester, and an adequate amount of pulverized flavor were mixed to homogeneity, and the resultant mixture was in an usual manner tabletted with a tablet machine into a tablet, about 350 mg in weight.

The product is an easily swallowable tablet with a satisfactory stability and without fear of cracking, and can be administered at a dose in the range of about 1–40 tablets/adult/day, preferably, in the range of about 2–20 tablets/adult/day. Such administration exerts a growth-promoting-effect on a microorganism of the genus Bifidobacterium, ard, similarly as the product in Example B-1, the product can be advantageously used in the control and promotion of health and beauty, the prevention of geriatric diseases, the promotion of recovery of health during and after diseases, and the prevention and treatment of diseases.

EXAMPLE B-10

Formula feed

A formula feed was prepared by mixing 40 parts by weight of a pulverized wheat bran, 38 parts by weight of defatted milk, 12 parts by weight of a powder having a high concentration of lactosucrose obtained by the method in Example A-3, 10 parts by weight of a vitamin preparation, 5 parts by weight of a fish powder, 5 parts by weight of calcium phosphate dibasic, 3 parts by weight of an oil and fat in liquid, 3 parts by weight of calcium carbonate, parts by weight of salt, and 2 parts by weight of a mineral preparation.

The product is a formula feed directed to domestic animals and fowls with an improved taste-quality, and particularly, it is favorably used for a young pig. Furthermore, the product exerts a growth-promoting-effect on a microorganism of the genus Bifidobacterium, and can be advantageously used for domestic animals in the prevention of infection and diarrhea, the promotion of appetite and fattening and the inhibition of an unpleasant smell caused by feces. In addition, if necessary, the product can be prepared into other formula feed by combining with other feed materials, for example, condensed feed materials such as cereal, wheat, starch, oil meal; rice bran and millers offal; and roughages such as straw, dried grass, bagasse and corncob.

Effect of the Invention

As described above, the present invention establishes an industrial-scale preparation of a lactosucrose high-content powder and use of said powder which have been impossible to attain. More particularly, the present invention establishes an industrial-scale preparation of a stable powder having a high concentration lactosucrose, said preparation comprising allowing a saccharide-transferring enzyme to act on an aqueous solution containing sucrose and lactose; removing concomitant saccharides in, the resultant. saccharide solution to obtain a solution having a high concentration of lactosucrose with a lactosucrose content of 45 w/w % or based on sugar composition; and spray-drying the resultant solution into a stable powder having a high concentration of lactosucrose. Furthermore, the present invention establishes an orally- or parenterally-administrable product in which the powder is incorporated.

The lactosucrose high-content powder thus obtained can be extensively used in orally- or parenterallyadministrable products as a selective saccharide source for a microorganism of the genus Bifidobacterium, as well as a sweetener, filler, stabilizer, viscosity imparting agent, crystalization-preventive agent for saccharides, humectant and gloss-imparting agent.

Furthermore, since the powder and products in which the powder is incorporated exert a growth-promoting-effect on a microorganism of the genus Bifidobacterium, they can play a role in the control and promotion of health, and can be advantageously used in the prevention of geriatric diseases, recovery of health during and after diseases, and the prevention and treatment of hyperammonemia and hepatic encephalopathy.

In addition, since the products according to the present invention can be advantageously used for animals such as domestic animals and fowls in the prevention of infection and diarrhea, the promotion of appetite, fattening and egg-laying, and the inhibition of the formation of unpleasant smell caused by feces, the present invention has a great significance in the industrial fields of health foods, pharmaceuticals and cosmetics.

While there has been described what is at present considered to be the preferred embodiments of the invention, it will be understood that various modifications may be made therein, and it is intended to cover in the appended claims all such modifications as fall within the true spirit and scope of the invention.

We claim:

1. A free-flowing powder containing a high concentration of lactosucrose having a moisture content lower than about 3% and obtained by the process of:
   (a) allowing a saccharide-transferring enzyme to act on an aqueous solution containing sucrose and lactose, wherein the ratio of said sucrose and lactose is in the range of about 1:10 to 10:1;
   (b) removing concomitant saccharides from the resultant saccharide solution containing lactosucrose to obtain a solution having a high concentration of lactosucrose with a lactosucrose content of 45 w/w%, d.s.b., or higher based on sugar composition; and
   (c) spray-drying the solution having a high concentration of lactosucrose into a free-flowing powder having a moisture content of less than about 3%.

2. In the process of promoting the selective growth of microorganisms of the genus Bifidobacterium in an animal in vivo by administering to the animal an effective amount of a selective saccharide source therefor, the improvement wherein said source is a freeflowing powder having a high concentration of lactosucrose in accordance with claim 1, and the dose of said free-flowing powder to said animal is in the range of 0.01–5.0 g/day/kg of the weight of said animal.

3. An orally- or parenterallyadministrable product produced by a process which comprises:
   (a) allowing a saccharide-transferring enzyme to act on an aqueous solution containing sucrose and lactose;
   (b) removing concomitant saccharides from the resultant saccharide solution containing lactosucrose to obtain a solution having a high concentration of lactosucrose with a lactosucrose content of 45 w/w%, d.s.b., or higher based on sugar composition;
   (c) spray-drying the solution having a high concentration of lactosucrose into a free flowing powder having a moisture content of less than about 3%; and
   (d) incorporating the resultant free-flowing powder having a high concentration of lactosucrose in an orally- or parenterally- administrative product.

4. In the process of promoting the selective growth of microorganisms of the genus Bifidobacterium in an animal in vivo by administering to the animal an effective amount of a product containing an effective amount of a saccharide source for promoting the selective growth of said microorganisms in said animal, the improvement wherein said product is a product in accordance with claim 3, and the dose of lactosucrose in said product to said animal is in the range of 0.01-5.0 g/day/kg of the weight of said animal.

5. The process of claim 4, wherein the content of lactosucrose in said product is at least about 0.1 w/w %.

6. The process according to claim 2 wherein the animal is a human.

7. The process according to claim 4 wherein the animal is a human.

* * * * *